United States Patent [19]
Sen et al.

[11] Patent Number: 6,063,973
[45] Date of Patent: May 16, 2000

[54] SYNTHESIS OF BRANCHED POLYETHYLENE FLUIDS FOR USE IN LUBRICANT COMPOSITIONS

[75] Inventors: Ayusman Sen, State College; Suzanne E. Schramm, Glen Mills; Jeffrey C. Trewella, Kennett Square, all of Pa.; Zhaozhong Jiang, Thorofare, N.J.; Gregory S. Long, State College, Pa.; Shahid Murtuza, Chicago, Ill.

[73] Assignees: Mobil Oil Corporation, Fairfax, Va.; The Pennsylvania University, University Park, Pa.

[21] Appl. No.: 09/272,410

[22] Filed: Mar. 19, 1999

Related U.S. Application Data

[60] Provisional application No. 60/078,695, Mar. 20, 1998.

[51] Int. Cl.$^7$ .............................. C10M 107/04; C07F 9/22
[52] U.S. Cl. .............................. 585/18; 585/10; 585/512; 585/522; 585/523; 585/530; 508/591; 526/144; 526/352
[58] Field of Search .................... 585/10, 18, 512, 585/522, 523, 524, 530; 508/591; 526/144, 352

[56] References Cited

U.S. PATENT DOCUMENTS

| | | | |
|---|---|---|---|
| 2,907,805 | 10/1959 | Bestian et al. | 260/683.15 |
| 2,993,942 | 7/1961 | White et al. | 260/683.15 |
| 3,168,588 | 2/1965 | White et al. | 260/683.15 |
| 3,474,157 | 10/1969 | White et al. | 260/683.15 |
| 3,594,443 | 7/1971 | Henrici et al. | 260/683.15 |
| 4,704,491 | 11/1987 | Tsutsui et al. | 585/10 |
| 4,827,064 | 5/1989 | Wu | 585/10 |
| 4,827,073 | 5/1989 | Wu | 585/530 |
| 4,914,254 | 4/1990 | Pelrine | 585/530 |
| 4,926,004 | 5/1990 | Pelrine et al. | 585/530 |
| 5,243,114 | 9/1993 | Johnson et al. | 585/530 |
| 5,260,500 | 11/1993 | Shiraki et al. | 585/524 |
| 5,506,184 | 4/1996 | Kissin et al. | 502/115 |
| 5,602,086 | 2/1997 | Le et al. | 508/591 |
| 5,744,679 | 4/1998 | Marinangeli et al. | 585/524 |
| 5,763,370 | 6/1998 | Doner et al. | 508/364 |
| 5,811,619 | 9/1998 | Commereuc et al. | 585/530 |
| 5,869,585 | 2/1999 | Mink et al. | 526/129 |
| 5,877,409 | 3/1999 | Girling | 73/54.06 |
| 5,962,761 | 10/1999 | Sechrest et al. | 585/524 |

FOREIGN PATENT DOCUMENTS

| | | |
|---|---|---|
| WO 9947628A | 3/1999 | European Pat. Off. . |

OTHER PUBLICATIONS

Henrici–Olivé, G. et al., "Oligomerization of Ethylene with Soluble Transition–Metal Catalysts", *Adv. Poly. Sci.*, 1974, 15, 1–30 month unavailable.

Kim, J.S. et al., "Novel Nickel(II) and Palladium(II)–Based Catalyst Systems for the Synthesis of Hyperbranched Polymers from Ethene", *J. Am. Chem. Soc.*, 1998, 120, 1932 month unavailable.

*Primary Examiner*—Jacqueline V. Howard
*Attorney, Agent, or Firm*—M. D. Keen

[57] ABSTRACT

The novel synthetic polyethylene fluids of the present invention are characterized by high viscosity indices (about 94–151 VI), low pour points (about –60 to –10° C.), and a kinematic viscosity of about 6 to 28 cSt KV at 100° C. The product compositions comprise polymers having a molecular weight of from about 300 to about 30,000 and a branching index of 151 to 586 branches per 1000 $CH_2$ groups, or BI=0.18–0.40. A process for preparing such novel synthetic polyethylene fluids comprises polymerizing ethylene in the presence of a catalyst system, said catalyst system comprising [A] and [B], wherein [A] is a catalyst having the formula $MX_5$ and [B] is a co-catalyst having the formula $R_nAlX_{3-n}$ where M is a Group VB, VIB, or VIII transition metal; X is a halogen anion; R is a $C_1$–$C_{20}$ alkyl group; and n is 1–2.

24 Claims, No Drawings

SYNTHESIS OF BRANCHED POLYETHYLENE FLUIDS FOR USE IN LUBRICANT COMPOSITIONS

This application claims benefit of U.S. Provisional Application Ser. No. 60/078,695, filed Mar. 20, 1998, the disclosure of which is hereby incorporated by reference in its entirety.

RELATED APPLICATIONS

The present invention is related to commonly assigned application Ser. No. 09/272,411, filed on Mar. 19, 1999, entitled "Synthesis of Branched Polyethylene Fluids For Use in Lubricant Compositions".

FIELD OF THE INVENTION

The present invention is directed to highly branched synthetic polyethylene fluids having a high viscosity index for use in lubricant compositions. The present invention is also directed to novel processes for polymerizing ethylene to obtain synthetic lube oils utilizing a novel catalyst system.

BACKGROUND OF THE INVENTION

Synthetic hydrocarbon fluids useful as lubricant compositions are well-known in the art. For example, one such synthetic hydrocarbon fluid is that obtained by the catalytic polymerization of α-olefins. In general, the synthetic lubricants provide lower friction and, hence, increase mechanical efficiency across the full spectrum of mechanical loads and do so over a wider range of operating conditions relative to mineral oil lubricants.

Synthetic lubricants made by polymerizing ethylene are especially desired because the raw materials are readily accessible and the process is overall more economically efficient. The production of polyethylene fluid is economically efficient because the production of polyethylene fluids is a single step process. In contrast, the production of poly α-olefin fluids, for example, requires ethylene to be first oligomerized to form the α-olefin.

The objective of industrial research on synthetic lubricants is, in general, to achieve a polymeric fluid that exhibits a useful viscosity over a wide range of temperature, i.e., has a good viscosity index (VI), while also exhibiting good lubricity, and a pour point equal to or better than mineral oil. One characteristic of the molecular structure of the polymeric fluids has been found to correlate very well with all of these desirable lubricant properties. This characteristic is the polymer's branching index, BI. BI is the ratio of methyl protons to total non-benzylic, aliphatic group protons in the polymer product and is easily determined from proton NMR spectra by calculating the ratio in percent of non-benzylic methyl hydrogens in the range of 0.5 to 1.05 ppm, to the total non-benzylic aliphatic hydrogens in the range of 0.5 to 2.1 ppm.

Generally, as the BI increases, the pour point of the polyethylene fluid, i.e., the temperature at which the composition changes from a liquid to a solid, decreases. This is a desirable effect as a lower pour point extends the application range of the polyethylene fluid. BI, however, has a negative effect on the viscosity index of a polyethylene oil; it is well-known in the art that the viscosity index of polyethylene fluids decreases as the branching index increases. This is an undesirable effect because a lower viscosity index indicates a poor viscosity-temperature performance. Thus, the challenge in synthesizing polyethylene fluids is to achieve an amount of branching sufficient to maintain the polyethylene in a liquid state such that the polyethylene fluid has a good viscosity index.

Polymerization of ethylene by transition metal catalysts, for example, usually leads to the formation of solid, linear polymers. As such, they are not suitable as soft materials or lubricants for most applications.

Recently, DuPont and the University of North Carolina, have developed novel Ni(II)- and Pd(II)-based catalysts which catalyze the polymerization of ethylene to form polyethylene liquids. These Nickel(II) and Palladium(II)-based catalysts contain chelating ligands which, as stated to, greatly reduce chain transfer termination rates and, thus, lead to the formation of high molecular weight polymers. In these systems, however, the degree of branching is only 20 to 150 branches per 1000 $CH_2$ groups.

Other highly active Nickel(II) and Palladium(II)-based catalysts have been discovered by Penn State University and have been employed for the preparation of highly-branched polyethylene fluids having greater than 587 branches per 1000 $CH_2$ groups. These polymers and their synthesis have been reported by J. S. Kim, J. H. Powlow, L. M. Wojcinski, S. Murtuza, S. Kacker, and A. Sen, "Novel Nickel(II) and Palladium(II)-Based Catalyst Systems for the Synthesis of Hyperbranched Polymers from Ethene," J. Am. Chem. Soc. 120, 1932, 1998. Such highly branched polymers, however, have a VI that typically is too low to be used as, for example, a lube basestock.

A report from Switzerland [Adv. Poly. Sci. 1974, 15, 1] describes the use of a $TiCl_4/EtAlCl_2$ catalyst for the polymerization of ethylene in benzene to give branched polymers. The products obtained, however, were of relatively low branching and molecular weight. One detrimental side reaction associated with the use of benzene solvent is Friedel-Crafts alkylation of the solvent and thus, a large portion of the product is reported to contain aromatic rings.

Thus, there is a need in the art for polyethylene fluids having a molecular weight, a branching index, and a viscosity index such that they are suitable for use as synthetic lubricants and processes for the manufacture of such polyethylene fluids.

SUMMARY OF THE INVENTION

The novel synthetic polyethylene fluids of the present invention are characterized by high viscosity indices (about 94–151 VI), low pour points (about −60 to −10° C.), and a kinematic viscosity of about 6 to 28 cSt KV at 100° C. The compositions comprise polymers having a molecular weight of from about 300 to about 30,000 and a branching index of 151 to 586 branches per 1000 $CH_2$ groups, or BI=0.18–0.40.

It has also been discovered that such novel synthetic polyethylene fluids can be prepared by polymerizing ethylene with a controlled catalyst system and under controlled temperatures with minimal formation of solid polyethylene byproduct.

In one embodiment of the present invention, the polyethylene fluids of the present invention are prepared by polymerizing ethylene in the presence of a catalyst system consisting of [A] and [B], wherein [A] is a catalyst having the empirical formula $MX_5$ and [B] is a co-catalyst having the empirical formula $R_nAlX_{3-n}$, where M is a Group VB, VIB, or VIII transition metal; X is a halogen anion; R is a $C_1$–$C_{20}$ alkyl group; and n is 1–2.

DETAILED DESCRIPTION OF THE INVENTION

The novel synthetic polyethylene fluids of the present invention are characterized by high viscosity indices (about 94–151 VI), low pour points (about –60 to –10° C.), and a kinematic viscosity of about 6 to 28 cSt KV at 100° C. as detailed in ASTM method D 445-5, herein incorporated by reference. The compositions comprise polymers having a molecular weight of from about 300 to about 30,000 and a branching index of 151 to 586 branches per 1000 $CH_2$ groups, or BI=0.18–0.40.

Preferably, the polyethylene fluids of the present invention are used as a component in a lubricating oil composition. More preferably, the polyethylene fluids of the present invention are used as a lube basestock (the primary component in a lubricant formulation). As used herein, the term "basestock" refers to a hydrocarbon oil without additives. Lube basestocks, prior to use as lubricants, are conventionally compounded with one or more additives such as antioxidants, anti-wear additives, extreme pressure additives, friction modifiers, viscosity index improvers, pour point depressants, detergents, dispersants, corrosion inhibitors, metal deactivators, seal compatibility additives, demulsifiers, anti-foam additives, mineral oils, synthetic PAO, esters, wax isomerates, polyalkylenes, alkylated aromatics, hydrocrackates, solvent-refined basestocks and mixtures thereof. It has been discovered that such novel synthetic polyethylene fluids can be prepared by polymerizing ethylene with a novel catalyst system with minimal formation of solid polyethylene byproduct.

As used and referred to herein, viscosity index (VI) represents a particular fluid's change of viscosity with temperature. A high VI indicates a relatively low rate of change of viscosity with temperature. Conversely, a low VI indicates a relatively high rate of change of viscosity with temperature. VI is measured according to ASTM Method D 567-41, herein incorporated by reference.

As used and referred to herein, branching index (BI) refers to the ratio of methyl protons to total non-benzylic, aliphatic group protons in the polymer product. BI is calculated as the ratio in percent of non-benzylic methyl hydrogens in the range of 0.5 to 1.05 ppm, to the total non-benzylic aliphatic hydrogens in the range of 0.5 to 2.1 ppm. For each measurement, 359.88 MHZ $^1H$ solution NMR spectra were obtained on a Bruker 360 MHZ AMX spectrometer using 10% solutions in $CDCl_3$.

As used and referred to herein, and unless otherwise specified, molecular weight refers to the actual molecular weight of the polymer. Molecular weight is measured on a Waters Associates liquid/gel permeation chromatograph (GPC) equipped with STYRAGEL™ columns and a differential refractometer detector using a polystyrene standard for calibration.

In one embodiment of the present invention, the polyethylene fluids described above are prepared by polymerizing ethylene in the presence of a catalyst system comprising [A] and [B], wherein [A] is a catalyst having the empirical formula $MX_5$ and [B] is a co-catalyst having the empirical formula $R_nAlX_{3-n}$, where M is a Group VB, VIB, or VIII transition metal; X is a halogen anion; R is a $C_1$–$C_{20}$ alkyl group; and n is 1–2.

Preferably, the catalyst [A] comprises a solid, soluble transition metal halide of a Group VB transition metal. More preferably, the metal, M, is Tantalum, $Ta^{5+}$. The halide, X, is selected from any of the halogens. Preferably, X is $Cl^-$ or $Br^-$.

The co-catalyst, [B], is a halogenated aluminum alkyl compound, the formula of which has been presented above. R is an alkyl group preferably having from about 1 to 20 carbon atoms, more preferably about 2 to 5 carbon atoms, most preferably about 2 carbon atoms.

The value of n represents an average value when aluminum sesqui-chloride (a mixture of aluminum diethyl chloride and aluminum ethyl dichloride) is used. It is essential that these halogenated derivatives be employed as contrasted to the hydrocarbon aluminum derivatives such as aluminum triethyl, aluminum triisobutyl, etc. The amount of solid polymer increases as the value of n goes from 1 to 2. Aluminum sesqui-chloride is preferred. An especially preferred compound is aluminum ethyl dichloride.

Preferably, the molar ratio of [A] to [B] is in the range of about 0.1 to 20. More preferably, the molar ratio of [A] to [B] is about 0.2 to 4. Most preferably, the molar ratio of [A] to [B] is about 1 to 1.

In practicing the process of the present invention, a solvent may optionally be employed. If a solvent is employed, it is preferred that the solvent is either a halogenated aromatic compound, an aliphatic hydrocarbon comprising from about 5 to about 20 carbons, or a mixture thereof. Examples of halogenated aromatic compounds are halogenated benzenes, such as chlorobenzene, dichlorobenzene, trichlorobenzene, bromobenzene, dibromobenzene, tribromobenzene, and alkylated halobenzenes having $C_1$–$C_{10}$ alkyl groups, such as, for example, p-chlorotoluene, and the like. Examples of aliphatic hydrocarbons comprising from about 5 to about 20 carbons are pentane, hexane, heptane, decane, and dodecane.

The polymerization temperature useful in carrying out the process of this invention is, for example, about –50° to 200° C., preferably about –30° to 150° C., more preferably about 20° to 120° C.

In another embodiment of the present invention, preferably at least one component of the catalyst system comprising [A] and [B] is supported by an inert support. More preferably, more that one component is supported by an inert support. Such inert supports are well known to those skilled in the art such as, for example, silica, alumina, carbon, zirconia, magnesia, diatomatious earth, kieselgur, and mixtures thereof. Supporting the components of the catalyst system comprising [A] and [B] to such inert support is accomplished by techniques well known to those skilled in the art such as, for example, impregnation.

The use of the described catalyst system comprising [A] and [B] for the polymerization of ethylene controls the amount of branching to obtain liquid polyethylene products having a high branching index consistent with the required viscosity index while maintaining fluid characteristics at a broad temperature application range, i.e., from about –60 to about –10° C.

In another embodiment of the present invention, the polymerization is carried out in the presence of a modifier such as hydrogen or a Lewis acid such as, for example, $FeCl_3$ or $AlCl_3$ in addition to the above described catalyst system comprising [A] and [B]. Without intending to be bound by any theory, it is believed that the addition of hydrogen, $FeCl_3$, or $AlCl_3$ lowers the molecular weight without significantly effecting the BI, the VI, or the pour point. Such modifiers are employed to create polyethylene compositions of the present invention that are suitable for use in a plurality of applications requiring a plurality of viscosities. If $AlCl_3$ is used as the modifier, preferably from about 0.1 to 100 moles, more preferably from about 1 to 75 moles, and most preferably about 5 to 20 moles of $AlCl_3$ is used. If $FeCl_3$ is used as the modifier, preferably from about 0.1 to 100 moles, more preferably from about 1 to 75 moles, and most preferably from about 5 to 20 moles of $FeCl_3$ is used. If $H_2$ is used as the modifier, it is preferable that it is used at a partial pressure of from about 1 to 500 psi, more preferably from about 5 to 50 psi.

In another embodiment of the present invention, highly-branched polyethylene fluids that are substantially free of methyl branches are prepared. In this embodiment, the highly-branched polyethylene fluids comprise branches that have greater than one carbon atom such as, for example, ethyl, propyl, butyl, amyl, and hexyl groups. Polyethylene fluids that have less than 5 methyl branches per 1000 $CH_2$ groups are prepared by polymerizing ethylene in the presence of a catalyst system comprising [C] and [B], wherein [C] is a catalyst having the empirical formula $MX_4$ and [B] is a co-catalyst having the empirical formula $R_nAlX_{3-n}$, where M is a Group IVB transition metal, X is a halogen anion, R is a $C_1$–$C_{20}$ alkyl group, and n is 1–2, in the presence of a promoter, wherein the promoter is selected from the group consisting of hydrogen or a Lewis acid such as, for example, $FeCl_3$, $AlCl_3$, or mixtures thereof.

Preferably, the catalyst [C] is a solid, soluble transition metal halide of a Group IVB transition metal. Preferably, the metal, M, is Titanium, $Ti^{4+}$. The halide, X, can be selected from any of the halogens. Preferably, X is $Cl^-$ or $Br^-$.

The co-catalyst, [B], is a halogenated aluminum alkyl compound, the formula of which has been presented above. R is an alkyl group preferably having from about 1 to about 20 carbon atoms, more preferably about 2 to 5 carbon atoms, most preferably about 2 carbon atoms.

The value of n represents an average value when aluminum sesqui-chloride (a mixture of aluminum diethyl chloride and aluminum ethyl dichloride) is used. It is essential that these halogenated derivatives be employed as contrasted to the hydrocarbon aluminum derivatives such as aluminum triethyl, aluminum triisobutyl, etc. The amount of solid polymer increases as the value of n goes from about 1 to 2. Aluminum sesqui-chloride is preferred. An especially preferred compound is aluminum ethyl dichloride.

Preferably, the molar ratio of [C] to [B] is in the range of about 0.1 to 20. More preferably, the molar ratio of [C] to [B] is about 0.75 to 10. Most preferably, the molar ratio of [C] to [B] is about 1 to 5.

In practicing the process of the present invention, a solvent may optionally be employed. If a solvent is employed, it is preferred that the solvent is either a halogenated aromatic compound, an aliphatic hydrocarbon comprising from about 5 to about 20 carbons, or a mixture thereof. Examples of halogenated aromatic compounds are halogenated benzenes, such as chlorobenzene, dichlorobenzene, trichlorobenzene, bromobenzene, dibromobenzene, tribromobenzene, and alkylated halobenzenes having $C_1$–$C_{10}$ alkyl groups, such as, for example, p-chlorotoluene, and the like. Examples of aliphatic hydrocarbons comprising from about 5 to about 20 carbons are pentane, hexane, heptane, decane, and dodecane.

If $AlCl_3$ is used as the promoter, preferably from about 0.1 to 100 moles, more preferably from about 5 to 50 moles, and most preferably about 15 to 25 moles of $AlCl_3$ is used. If $FeCl_3$ is used as the promoter, preferably from about 0.1 to 50 moles, more preferably from about 0.5 to 5 moles, and most preferably from about 1 to 3 moles of $FeCl_3$ is used. If $H_2$ is used as the promoter, it is preferable that it is used at a partial pressure of from about 1 to 200, more preferably from about 5 to 50 psi, and most preferably from about 10 to 30 psi.

The polymerization temperature useful in carrying out the process of this invention is, for example, about –50° to 200° C., preferably about –30° to 150° C., more preferably about 20° to 120° C.

In another embodiment of the present invention, preferably at least one component of the catalyst system comprising [C] and [B] is supported by an inert support. More preferably, more than one component is supported by an inert support. Such inert supports are well known to those skilled in the art such as, for example, silica, alumina, carbon, zirconia, magnesia, diatomatious earth, kieselgur, and mixtures thereof. Supporting the components of the catalyst system comprising [C] and [B] is accomplished by techniques well known to those skilled in the art such as, for example, impregnation.

The use of the described catalyst system comprising [C] and [B] in the presence of hydrogen or a Lewis acid for the polymerization of ethylene controls the type of branching to obtain liquid polyethylene products only. The resultant liquid polyethylene fluids have no methyl branches and have a high branching index consistent with the required viscosity index while maintaining fluid characteristics at a broad temperature application range, i.e., from bout –60 to about –10° C. In addition, the use of the described catalyst system comprising [C] and [B] in the presence of hydrogen or a Lewis acid for the polymerization of ethylene eliminates the formation of solid polyethylene.

The following examples further illustrate additional objects, advantages, and novel features of this invention. It will become apparent to those skilled in the art, however, that such examples are not intended to limit the scope of the invention.

EXAMPLES

Materials and General Methods

Example 1

C.P. or higher grade chemicals were used as received unless otherwise noted. Ethylaluminum dichloride was obtained as 1 M solution in hexane and was used directly with the solvent. Chlorobenzene and hexane used for ethylene polymerization were dried over calcium hydride, vacuum distilled, and stored under nitrogen.

All catalysts manipulations were performed in a nitrogen-filled glovebox.

Molecular weights of polymers were measured on a Waters Associates liquid/gel permeation chromatograph (GPC) equipped with STYRAGEL™ columns and a differential refractometer detector as follows:

(1) Polystyrene standards were used for calibration.
(2) The GPC count of the standard polystyrene of known molecular weight, M, is measured, and a calibration curve for the molecular weight, M, versus the elution volume is drawn.
(3) A gel permeation chromatograph of a sample polymer is taken by GPC measurement. From the calibration curve mentioned in (2) above, the number average molecular weight, $M_n$, and the weight average molecular weight, $M_w$, of the sample are calculated. The $M_w/M_n$ is thus obtained.

Measurement of Branching Characteristics

Example 2

Branching Index (BI or $H_{Me}/H_{tot}$). For each PE fluid, 359.88 MHZ $^1$H solution NMR spectra were obtained on a Bruker 360 MHZ AMX spectrometer using 10% solutions in $CDCl_3$. TMS was the internal chemical shift reference. $CDCl_3$ solvent gives a peak located at 7.28. All spectra were obtained under quantitative conditions using 90 degree pulse (10.9 μs) with a pulse delay time of 30 s, which is at least five times the longest hydrogen spinlattice relaxation time (T1), and 120 scans to ensure good signal-to-noise.

H atom types were defined according to the following regions:

9.2–6.2 ppm hydrogens on aromatic rings;
6.2–4.0 ppm hydrogens on olefinic carbon atoms;
4.0–2.1 ppm benzylic hydrogens at the α-position to aromatic rings;
2.1–1.4 ppm paraffinic CH methine hydrogens;
1.4–1.05 ppm paraffinic $CH_2$ methylene hydrogens;
1.05–0.5 ppm paraffinic $CH_3$ methyl hydrogens.

The BI was calculated as the ratio in percent of non-benzylic methyl hydrogens in the range of 0.5 to 1.05 ppm, to the total non-benzylic aliphatic hydrogens in the range of 0.5 to 2.1 ppm.

Branching Proximity is a measurement of the branch distribution along a carbon chain. For each polyethylene lube stock, 90.5 MHZ $^{13}$C NMR single pulse and 135 Distortionless Enhancement by Polarization Transfer (DEPT) NMR spectra were obtained on a Bruker 360 MHZ AMX spectrometer using 10% solutions in $CDCl_3$. TMS was the internal chemical shift reference. $CDCl_3$ solvent gives a triplet located at 77.23 ppm in the $^{13}$C spectrum. All single-pulse spectra were obtained under quantitative conditions using 45 degree pulses (6.3 μs) and a pulse delay time of 60 s, which is at least five times the longest carbon spin-lattice relaxation time (T1), to ensure complete relaxation of the sample, and 200 scans to ensure good signal-to-noise, and WALTZ-16 proton decoupling.

The C atom types $CH_3$, $CH_2$, and CH were identified from the 135 DEPT $^{13}$C NMR experiment. A major $CH_2$ resonance in all $^{13}$C NMR spectra at 29.8 ppm is due to equivalent recurring methylene carbons which are four or more removed from an end group or branch ($CH_2$>4). The types of branches were determined based primarily on the $^{13}$C chemical shifts for the methyl carbon at the end of the branch or the methylene carbon one removed from the methyl on the branch.

$TiCl_4/EtAlCl_2$ Catalyzed Synthesis of Branched Polyethylene (PE) Fluids

Example 3

$H_2$ as the Promoter

In a glass autoclave liner equipped with a Teflon-coated magnetic stir bar, $TiCl_4$ (38 mg, 0.20 mmol) was dissolved in 40 ml of chlorobenzene to form a yellow solution. Ethylaluminum dichloride (1.00 ml of 1M solution in hexane, 1.00 mmol) was then added and the solution turned a darker yellow. The 300 ml stainless steel autoclave was assembled under nitrogen, charged with 10 psi of hydrogen, exposed to a constant 50 psi feed of ethylene, and stirred at room temperature for 16 h. At the end of this period, the autoclave was vented and a small amount of methanol was added to deactivate the catalyst. After being diluted with chloroform (40 ml), the produce mixture was filtered and passed through neutral alumina to remove the catalyst residue Liquid PE was obtained upon complete removal of the solvents and light ethylene oligomers through distillation of the eluent under 0.1 torr vacuum at ambient temperature. The results on PE yield and structures are summarized in Table 1.

Example 4

H2 as the Promoter

A procedure analogous to the one described in Example 3 was performed using 10 ml of chlorobenzene and a 125 ml stainless steel autoclave. The reaction was allowed to take place for 12 h. The results on PE yield and structures are summarized in Table 1.

Example 5

$FeCl_3$ as the Promoter

In a glass autoclave liner equipped with a Teflon-coated magnetic stir bar, $TiCl_4$ (38 mg, 0.20 mmol) was dissolved in 10 ml of chlorobenzene to form a yellow solution. Ethylaluminum dichloride (1.00 ml of 1M solution in hexane, 1.00 mmol) and $FeCl_3$ (0.2 mmol) were then added. The 125 ml stainless steel autoclave was assembled under nitrogen, exposed to a constant 50 psi feed of ethylene, and stirred at room temperature for 12 h. At the end of this period, the autoclave was vented and small amount of methanol was added to deactivate the catalyst. The liquid product mixture was diluted with chloroform (40 ml) and passed through neutral alumina to remove the catalyst residue. Liquid PE was obtained upon complete removal of the solvents and light ethylene oligomers through distillation of the eluent under 0.1 torr vacuum at ambient temperature. The results on PE yield and structures are summarized in Table 1.

Example 6

$AlCl_3$ as the Promoter

A procedure analogous to the one described in Example 5 was performed using hexane (10 ml) as solvent instead of chlorobenzene, $EtAlCl_2$ (0.2 mmol) as cocatalyst, and $AlCl_3$ (4 mmol) as selectivity promoter instead of $FeCl_3$. The reaction was allowed to take place for 17 h. The results on PE yield and structures are summarized in Table 1.

$TaCl_5EtAlCl_2$, Catalyzed Synthesis of Branched Polyethylene (PE) Fluids

Example 7

In a glass autoclave liner equipped with a Teflon-coated magnetic stir bar, $TaCl_5$ (72 mg, 0.20 mmol) and ethylaluminum dichloride (0.20 ml of 1M solution in hexane, 0.2 mmol) were co-dissolved in 10 ml of chlorobenzene. The 125 ml stainless steel autoclave was then assembled under nitrogen, heated to 45° C., and exposed to a constant 700 psi feed of ethylene. The reaction mixture was stirred at 45° C.

for 16 h. At the end of this period, the autoclave was vented and a small amount of methanol was added to deactivate the catalyst. The resultant product mixture was diluted with chloroform (40 ml), filtered, and passed through neutral alumina or silica to remove the catalyst residue. Liquid PE was obtained upon complete removal of the solvents and light ethylene oligomers through distillation of the eluent under 0.1 torr vacuum at ambient temperature. No solid PE byproduct was formed. The results on liquid PE yield and structures are summarized in Table 2.

Examples 8 and 9

The procedure of Example 7 was repeated at reaction temperatures 25° C. and 75° C., respectively. The results on liquid PE yield and structures are summarized in Table 2.

Example 10

A procedure analogous to the one described in Example 7 was performed using hexane, instead of chlorobenzene, as solvent. The results on liquid PE yield and structures are summarized in Table 2.

Example 11

A procedure analogous to the one described in Example 7 was performed using EtAlCl$_2$ (0.2 mmol) cocatalyst along with AlCl$_3$ (2.00 mmol) as selectivity modifier. The results on PE yield and structures are summarized in Table 2.

Example 12

A procedure analogous to the one described in Example 7 was performed. The autoclave reactor was charged with 10 psi of hydrogen before it was heated and exposed to a constant 700 psi feed of ethylene. The results on PE yield and structures are summarized in Table 2.

Example 13

A mixture of TaCl$_5$ (27 mg, 0.075 mmol) and EtAlCl$_2$ (0.131 ml of 1M solution in hexane, 0.131 mmol) in 10 ml of chlorobenzene was placed in a 125 ml autoclave. The autoclave reactor was charged with 750 psi of ethylene and stirred at 40° C. for 18 h. At the end of this period, the unreacted ethylene was vented and the product mixture was filtered. A viscous oil (4.0 g) was obtained after the filtrate was evaporated under vacuum (0.1 torr) at ambient temperature to remove the solvent and low molecular weight ethylene oligomers. Liquid PE: $M_n$=1350, $M_w$=1750, $M_w/M_n$=1.3, $H_{Me}/H_{tot}$=0.29.

Example 14

A mixture of TaCl$_5$ (0.80 mmol) and EtAlCl$_2$ (312 (0.80 mmol) in 40 ml of chlorobenzene was placed in a 300 ml autoclave. The autoclave reactor was stirred, heated to 115° C., and exposed to a constant 700 psi feed of ethylene for 16 h. At the end of this period, the ethylene feed was stopped and the unreacted ethylene was vented. The reaction was quenched with 5 ml of methanol, and the product mixture was diluted with CHCl$_3$ (80 ml) and filtered. The filtrate was eluted over silica to remove the catalyst residue. The product (20 g) was obtained after evaporation of the eluent at 120° C. under vacuum (0.1 torr) to remove the solvents and low molecular weight ethylene oligomers. Liquid PE: $M_n$=500, $M_w$=820, $M_w/M_n$=1.6, $H_{Me}/H_{tot}$=0.34.

Examples 15 and 16

Two procedures analogous to the one described in Example 7 were performed. Et$_3$Al$_2$Cl$_3$ (0.10 mmol) and Et$_2$AlCl (0.20 ml of 1M solution in hexane, 0.20 mmol) were used as co-catalyst, respectively, instead of EtAlCl$_2$. The results on PE yield and structures are summarized in Table 3.

Branching Structures and Physical Properties of PE Fluids

Examples 17 and 18

Branched PE fluids, prepared according to the procedures described above, were further distilled at 120° C. under vacuum (0.1 torr) to remove non-lube fractions. Tables 4 and 5 show the physical properties and corresponding branching structures of the heavy fractions. As shown in Table 4, the heavy lube fractions of the polyethylene oils prepared according to Examples 3 and 14, in particular, exhibit excellent lube characteristics.

Comparative Examples

Comparative Example 1

TiCl$_4$/EtAlCl$_2$/C$_6$H$_5$Cl Catalyzed Synthesis of Branched Polyethylene (PE) Fluids. A procedure analogous to the one described in Example 4 was performed. No hydrogen was used during the reaction. The results on PE yield and structures are summarized in Table 1.

Comparative Example 2

TiCl$_4$/EtAlCl$_2$/Hexane Catalyzed Synthesis of Branched Polyethylene (PE). A procedure analogous to the one described in Example 4 was performed. The reaction was carried out in hexane (10 ml), instead of chlorobenzene, and in the absence of hydrogen The results on PE yield and structures are summarized in Table 1.

TABLE 1

| | | | | | | | | | | |
|---|---|---|---|---|---|---|---|---|---|---|
| TiCl$_4$/EtAlCl$_2$ Catalyzed Polymerization of Ethylene[a] | | | | | | | | | | |
| | EtAlC$_2$/ TiCl$_4$[b] | Promoter | Solvent | RXN Time (h) | Liquid PE (g)[c] | (Solid PE, g)[c] | $M_n$[d] | $M_w$[d] | $M_w/M_n$[d] | HM$_e$/H$_{tot}$ |
| Example (Ex.) | | | | | | | | | | |
| 3 | 5 | H$_2$ (10 psi) | C$_6$H$_5$Cl (40 ml) | 16 | 18.9 | 0 | 910 | 1300 | 1.4 | 0.25 |
| 4 | 5 | H$_2$ (10 psi) | C$_6$H$_5$Cl (10 ml) | 12 | 4.5 | 0 | 850 | 1300 | 1.5 | 0.23 |
| 5 | 5 | 1 FeCl$_3$ | C$_6$H$_5$Cl (10 ml) | 12 | 4.5 | 0 | 950 | 1320 | 1.4 | 0.23 |
| 6 | 1 | 2 AlCl$_3$ | hexane (10 ml) | 17 | 3.7 | 0 | 1140 | 1560 | 1.4 | 0.23 |

TABLE 1-continued

TiCl$_4$/EtAlCl$_2$ Catalyzed Polymerization of Ethylene[a]

| | EtAlC$_2$/ TiCl$_4$[b] | Promoter | Solvent | RXN Time (h) | Liquid PE (g)[c] | (Solid PE, g)[c] | M$_n$[d] | M$_w$[d] | M$_w$/M$_n$[d] | HM$_e$/H$_{tot}$ |
|---|---|---|---|---|---|---|---|---|---|---|
| Comparative Ex. | | | | | | | | | | |
| 1 | 5 | none | C$_6$H$_5$Cl (10 ml) | 12 | 3 | 1.3 | 920 | 1420 | 1.5 | 0.23 |
| 2 | 5 | none | hexane (10 ml) | 12 | trace | 4.6 | | | | |

[a]All reactions were carried out at ambient temperature and under 50 psi constant ethylene pressure using 0.20 mmol of TiCl$_4$
[b]Molar ratio
[c]Obtained after removal of solvent and light ethylene oligomers at 25° C. under vacuum (0.1 torr).
[d]Determined by GPC using polystyrene standards

TABLE 2

TaCl$_5$/EtAlCl$_2$ Catalyzed Polymerization of Ethylene[a]

| Example | EtAlCl$_2$/ TaCl$_5$[b] | Modifier | Solvent | Temp. ° C. | Liquid PE (g)[c] | M$_n$[d] | M$_w$[d] | M$_w$/M$_n$[d] | H$_{Me}$/H$_{tot}$ |
|---|---|---|---|---|---|---|---|---|---|
| 7 | 1 | none | C$_6$H$_5$Cl (10 ml) | 45 | 4.2 | 1310 | 2070 | 1.6 | 0.30 |
| 8 | 1 | none | C$_6$H$_5$Cl (10 ml) | 25 | 2.7 | 2040 | 3870 | 1.9 | 0.33 |
| 9 | 1 | none | C$_6$H$_5$Cl (10 ml) | 75 | 5.6 | 890 | 1310 | 1.5 | 0.27 |
| 10 | 1 | none | Hexane (10 ml) | 45 | 1.4 | 970 | 1300 | 1.3 | 0.40 |
| 11 | 1 | 10 AlCl$_3$ | C$_6$H$_5$Cl (10 ml) | 45 | 4.1 | 1060 | 1590 | 1.5 | 0.40 |
| 12 | 1 | H$_2$ (10 psi) | C$_6$H$_5$Cl (10 ml) | 45 | 4.4 | 1010 | 1440 | 1.4 | 0.31 |

[a]All reactions were carried out under 700 psi of ethylene 16 h using 0.20 mmol of TiCl$_5$
[b]Molar ratio
[c]Obtained after removal of solvent and light ethylene oligomers at 25° C. under vacuum (0.1 torr).
[d]Determined by GPC using polystyrene standards

TABLE 3

Co-catalyst Effect on the Ethylene Polymerization Catalyzed by TaCl$_5$[a]

| Example | Cocatalyst (Equiv. vs TaCl$_5$) | Solvent | Temp. (° C.) | Liquid PE (g)[c] | M$_N$[c] | M$_W$[c] | M$_W$/M$_N$[c] | H$_{Me}$/H$_{tot}$ |
|---|---|---|---|---|---|---|---|---|
| 7 | 1 EtAlCl$_2$ | C$_6$H$_5$Cl (10 ml) | 45 | 4.2 | 1310 | 2070 | 1.6 | 0.30 |
| 15 | 0.5 Et$_3$Al$_2$Cl$_3$ | C$_6$H$_5$Cl (10 ml) | 45 | 2.4 | 1780 | 3080 | 1.7 | 0.32 |
| 18 | 1 Et$_2$AlCl | C$_6$H$_5$Cl (10 ml) | 45 | 2.5 | 920 | 1410 | 1/5 | 0.32 |

[a]All reactions were carried out under 700 psi ethylene for 16 H using 0.20 mmol of TiCl$_5$
[b]Obtained after removal of solvent and light ethylene oligomers at 25° C. under vacuum (0.1 torr).
[c]Determined by GPC using polystyrene standards

TABLE 4

Physical Properties of the PE Lube Stocks

| Heavy PE Fraction of Ex.[a] | 7 | 8 | 13[b] | 3 | 14 |
|---|---|---|---|---|---|
| Lube Yield, wt %[c] | —[d] | —[d] | —[d] | 92 | 56 |
| KV, cST @ 100° C. | 15.17 | 28.20 | 12.94 | 9.595 | 6.343 |
| KV, CST @ 40° C. | 143.6 | 415.1 | 85.46 | 58.99 | 40.86 |
| Viscosity Index | 107 | 94.2 | 151 | 146 | 103 |
| PP (° C.) | −30 | −10 | −35 | −24 | −60 |

[a] Obtained after distilling off light hydrocarbon fraction at 120° C. under vacuum (0.1 torr).
[b] Containing 14 wt % distillate fraction with <650° F. boiling point
[c] Yield of 650° F. + distillate fraction vs total amount of ethylene converted
[d] Undetermined

TABLE 5

Branching Structures of the PE Lube Stocks

| Heavy PE Fraction of Ex. | 7 | 8 | 4 | 7 | 3 |
|---|---|---|---|---|---|
| % Different Proton | | | | | |
| % CH$_3$ | 33.8 | 40.5 | 24.6 | 34.1 | 26.3 |
| % CH$_2$ | 55.7 | 498 | 69.5 | 59 | 65.8 |
| % CH | 8.4 | 8.1 | 4.2 | 6.1 | 5.5 |
| % Olefin | 0.7 | 0.4 | 1.7 | 0.7 | 2.4 |
| BI | 34.5 | 41.2 | 25 | 34.4 | 26.9 |
| Branches Per 1000 CH$_2$ | | | | | |
| Methyl | 69 | 91 | 0 | 68 | 0 |
| Ethyl | 01 | 64 | 36 | 7 | 41 |
| Propyl | 30 | 73 | 4 | 38 | 8 |
| Butyl | 20 | 51 | 39 | 36 | 40 |
| Amyl | 34 | 25 | 2 | 27 | 10 |

TABLE 5-continued

Branching Structures of the PE Lube Stocks

| Heavy PE Fraction of Ex. | 7 | 8 | 4 | 7 | 3 |
|---|---|---|---|---|---|
| Hexyl+ | 65 | 36 | 81 | 59 | 91 |
| Branching Proximity, % $CH_2 > 4$ | 6.3 | 1.5 | 21.6 | 6.4 | 15.8 |

While the present invention has been described in connection with the various Examples, it is to be understood that other embodiments may be used or modifications and additions may be made to the described embodiment for performing the same function of the present invention without deviating therefrom. Therefore, the present invention should not be limited to any single embodiment, but rather should be construed in breadth and scope in accordance with the recitation of the appended claims.

What is claimed is:

1. A liquid polyethylene composition having 151 to 586 branches per 1000 $CH_2$ groups and a molecular weight between about 300 and about 30,000.

2. The liquid polyethylene composition of claim 1 having about 160 to 570 branches per 1000 $CH_2$ groups.

3. The liquid polyethylene composition of claim 2 having about 300 to 400 branches per 1000 $CH_2$ groups.

4. A lube basestock composition comprising a liquid polyethylene composition of claim 1.

5. The liquid polyethylene composition of claim 1 having a viscosity index between about 94 and about 151.

6. The liquid polyethylene composition of claim 5 wherein the viscosity index is between about 120 and 150.

7. The liquid polyethylene composition of claim 1 having a pour point of from about −60 to about −10° C.

8. A process for preparing a liquid polyethylene composition having 151 to 586 branches per 1000 $CH_2$ groups and a molecular weight between about 300 and about 30,000 from ethylene, said process comprising:

polymerizing ethylene in the presence of a catalyst system, said catalyst system comprising [A] and [B], wherein [A] is a catalyst having the formula $MX_5$ and [B] is a co-catalyst having the formula $R_nAlX_{3-n}$ where M is a Group VB transition metal;

X is a halogen;

R is a $C_1$–$C_{20}$ alkyl group; and n is 1–2.

9. The process of claim 8 wherein said polymerization step is performed in the presence of a solvent.

10. The process of claim 9 wherein the solvent is a halogenated aromatic compound.

11. The process of claim 10 wherein the halogenated aromatic compound is selected from the group consisting of chlorobenzene, dichlorobenzene, trichlorobenzene, and mixtures thereof.

12. The process of claim 9 wherein the solvent is an aliphatic hydrocarbon comprising from about $C_5$–$C_{20}$ paraffins or mixtures thereof.

13. The process of claim 8 wherein said at least one component of said catalyst system is supported on an inert support.

14. The process according to claim 13 wherein said inert support is selected from the group consisting of silica, alumina, carbon, zirconia, magnesia, diatomatious earth, kieselgur, and mixtures thereof.

15. The process of claim 8 performed in the presence of a Lewis acid.

16. The process of claim 15 wherein the Lewis acid is $AlCl_3$ or $FeCl_3$.

17. The process of claim 8 wherein the Group VB transition metal is $Ta^{5+}$.

18. The process of claim 8 wherein the molar ratio of [A] to [B] is 0.1 to 10.

19. The process of claim 18 wherein the molar ratio of [A] to [B] is 1 to 1.

20. The polyethylene fluid prepared by the process of claim 8.

21. A synthetic lubricant basestock comprising the polyethylene fluid of claim 20.

22. A lubricating oil composition, comprising a liquid hydrocarbon composition prepared by the process of claim 8 as a lubricating oil basestock; and optionally, effective amounts of lubricating oil additives selected from the group consisting of antioxidants, anti-wear additives, extreme pressure additives, friction modifiers, viscosity index improvers, pour point depressants, detergents, dispersants, corrosion inhibitors, metal deactivators, seal compatibility additives, demulsifiers and anti-foam additives and mixtures thereof.

23. The lubricating oil composition of claim 22, further comprising an additional lubricating oil basestock selected from the group consisting of a mineral oil, synthetic PAO, esters, wax isomerates, polyalkylenes, alkylated aromatics, hydrocrackates and solvent-refined basestocks.

24. The lubricating oil composition of claim 23, wherein said liquid hydrocarbon composition is present at a concentration level of at least 5 wt % of the total lubricating oil basestock composition.

* * * * *